(12) United States Patent
Hayashi et al.

(10) Patent No.: US 8,735,163 B2
(45) Date of Patent: May 27, 2014

(54) BLOOD COAGULATION SYSTEM ANALYZING METHOD AND BLOOD COAGULATION SYSTEM ANALYZING DEVICE

(75) Inventors: Yoshito Hayashi, Chiba (JP); MarcAurele Brun, Tokyo (JP); Shinji Omori, Tokyo (JP); Yoichi Katsumoto, Tokyo (JP); Kazumasa Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 11 days.

(21) Appl. No.: 13/403,652

(22) Filed: Feb. 23, 2012

(65) Prior Publication Data

US 2012/0238026 A1    Sep. 20, 2012

(30) Foreign Application Priority Data

Mar. 17, 2011 (JP) ................................. 2011-058810

(51) Int. Cl.
  *G01N 33/86* (2006.01)
  *G01N 33/48* (2006.01)
(52) U.S. Cl.
  USPC ............. 436/69; 436/63; 436/149; 436/150; 422/73; 422/82.01; 435/13; 73/64.41; 600/369
(58) Field of Classification Search
  USPC ............. 436/63, 69, 149, 150; 422/68.1, 73, 422/82.01, 82.02; 435/13; 600/369; 73/64.41
  See application file for complete search history.

(56) References Cited

U.S. PATENT DOCUMENTS

| 6,432,657 | B1 * | 8/2002 | Kikuchi et al. ................. 435/13 |
| 2008/0063566 | A1 * | 3/2008 | Matsumoto et al. ......... 422/68.1 |
| 2009/0226412 | A1 * | 9/2009 | Yasuhiro et al. ........... 424/94.64 |
| 2012/0035450 | A1 * | 2/2012 | Hayashi ........................ 600/369 |
| 2012/0048732 | A1 * | 3/2012 | Hayashi et al. .......... 204/403.02 |

FOREIGN PATENT DOCUMENTS

| EP | 2 375 244 A1 | 10/2011 |
| JP | 2010-181400 | 8/2010 |
| RU | 1720386 | * 3/1995 |
| RU | 2061952 | * 6/1996 |
| WO | 2005/007868 A2 | 1/2005 |

OTHER PUBLICATIONS

A. S. Trask et al.; Warfarin initiation and monitoring with dotting factors II, VII, and X; The Annals of Pharmacotherapy; vol. 38; Dec. 30, 2003; pp. 251-256; USA.
Hayashi Yoshihito et al.; Dielectric Coagulometry: A New Approach to Estimate Venous Thrombosis Risk; Analytical Chemistry; vol. 82, No. 23; Dec. 1, 2010; pp. 9769-9774.
E. Maurer-Spurej and D. V. Devine; Platelet Aggregation Is Not Initiated by Platelet Shape Change; Laboratory Investigation; vol. 81, No. 11; Nov. 2001.
Yoshihito Hayashi et al.; Temporal variation of dielectric properties of preserved blood; Physics in Medicine and Biology, Taylor and Francis Ltd., London, GB; vol. 53, No. 1; Jan. 7, 2008; pp. 295-304.
T. Chelidze; Dielectric spectroscopy of blood; Journal of Non-Crystalline SOlids, North-Holland Physics Publishing, Amsterdam, NL; vol. 305, No. 1-3; Jul. 1, 2002; pp. 285-294.
European Search Report dated May 23, 2012, in connection with counterpart EP Application No. 12 00 1027.

* cited by examiner

*Primary Examiner* — Maureen Wallenhorst
(74) *Attorney, Agent, or Firm* — Dentons US LLP

(57) ABSTRACT

A blood coagulation system analyzing method includes acquiring information relating to the coagulability of blood based on a change generated in a complex permittivity spectrum measured in a coagulation process of the blood due to addition of a substance that activates or inactivates platelets to the blood.

13 Claims, 4 Drawing Sheets

BLOOD COAGULATION SYSTEM ANALYZING METHOD AND BLOOD COAGULATION SYSTEM ANALYZING DEVICE

BACKGROUND

The present technique relates to blood coagulation system analyzing methods and blood coagulation system analyzing devices. Specifically, the present technique relates to a blood coagulation system analyzing method to acquire information relating to the blood coagulability based on a complex permittivity spectrum measured in the coagulation process of blood.

Patients or healthy people having the risk of thrombosis are prophylactically dosed with an anti-platelet aggregation drug or an anticoagulant. Examples of the patients having the thrombus risk include patients with diabetes, arteriosclerosis, cancer, heart disease, and respiratory disease, perioperative patients, and patients currently taking an immunosuppressant. Examples of the healthy people having the thrombus risk include pregnant women and elderly people. The acetylsalicylic acid etc. is used as the anti-platelet aggregation drug. Warfarin, heparin, an activated blood coagulation factor X (Factor Xa) inhibitor, etc. is used as the anticoagulant.

In the prophylactic administration of the anti-platelet aggregation drug or the anticoagulant against the thrombosis, there is a side effect that an excessive dosage increases the bleeding risk. To obtain a sufficient prophylactic effect with prevention of this side effect, administration of medication in which the blood coagulability of the drug recipient is timely evaluated and the drug and the dosage are properly selected and set is necessary.

As the blood coagulability test, there are methods such as the prothrombin time-international normalized ratio (PT-INR) and the activated partial thromboplastin time (APTT). As the platelet aggregability test, there is a method in which a substance that induces platelet aggregation is added to platelet rich plasma (PRP) obtained by centrifugation of blood and a change in the light transmittance or the light absorbance in association with the aggregation is measured to thereby determine whether or not the aggregability is good.

Regarding the present technique, Japanese Patent Laid-open No. 2010-181400 (hereinafter, Patent Document 1) discloses a technique to acquire information relating to blood coagulation from the permittivity of blood, and describes a "blood coagulation system analyzing device having a pair of electrodes, an applying section that applies an alternating voltage to the pair of electrodes at a predetermined time interval, a measuring section that measures the permittivity of blood disposed between the pair of electrodes, and an analyzing section that analyzes the degree of the action of the blood coagulation system by using the permittivity of the blood measured at the time interval after the effect of an anticoagulant on the blood is released." In this blood coagulation system analyzing device, the early action of the blood coagulation system can be analyzed based on time change of the permittivity before the start timing of coagulation of the blood in terms of dynamics of viscoelasticity.

SUMMARY

In the related-art blood coagulability test such as PT-INR and APTT, substantially only the bleeding risk associated with blood hypocoagulability due to excessive administration of an anticoagulant can be evaluated but the thrombus risk associated with blood hypercoagulability cannot be evaluated. Furthermore, in the existing platelet aggregability test by use of PRP, the centrifugation procedure is essential. In addition, an accurate test result is not obtained due to activation of the platelets in this procedure and the operation is also cumbersome.

There is a need for the present technique to provide a blood coagulation system analyzing method capable of easily evaluating both blood hypercoagulability and hypocoagulability by using whole blood.

According to an embodiment of the present technique, there is provided a blood coagulation system analyzing method including acquiring information relating to the coagulability of blood based on a change generated in a complex permittivity spectrum measured in a coagulation process of the blood due to addition of a substance that activates or inactivates platelets to the blood.

In this blood coagulation system analyzing method, if a platelet activating substance is used as the substance, information relating to the aggregability of the platelets included in the blood in an inactive state can be acquired based on a change generated in the complex permittivity spectrum in association with platelet activation by the substance.

Furthermore, if a platelet inactivating substance is used as the substance, information relating to the aggregability of the platelets included in the blood in an active state can be acquired based on a change generated in the complex permittivity spectrum in association with platelet inactivation by the substance.

This blood coagulation system analyzing method is favorably used for evaluating drug efficacy in a subject to which an anti-platelet aggregation drug and/or an anticoagulant such as acetylsalicylic acid, warfarin, heparin, and an activated blood coagulation factor X inhibitor is administered.

According to another embodiment of the present technique, there is provided a blood coagulation system analyzing device including an analyzing section configured to determine the coagulability of blood based on difference in a spectrum pattern between a complex permittivity spectrum measured in a coagulation process of the blood to which a substance that activates or inactivates platelets is added and a complex permittivity spectrum measured in a coagulation process of the blood to which the substance is not added.

In the embodiments of the present technique, the term "complex permittivity" encompasses also electrical quantities equivalent to the complex permittivity. Examples of the electrical quantity equivalent to the complex permittivity include complex impedance, complex admittance, complex capacitance, and complex conductance. They can be converted to each other by simple electrical quantity conversion. Furthermore, measurement of the "complex permittivity" encompasses also measurement of only the real part or only the imaginary part.

The embodiment of the present technique provides a blood coagulation system analyzing method capable of easily evaluating both blood hypercoagulability and hypocoagulability by using whole blood.

DETAILED DESCRIPTION OF THE PREFERRED EMBODIMENT

A preferred embodiment for carrying out the present technique will be described below with reference to the drawings. The embodiment described below shows one example of representative embodiments of the present technique and the scope of the present technique is not narrowly interpreted due to it. The order of the description is as follows.
1. Blood Coagulation System Analyzing Method
   (1) Measurement Procedure
   (2) Analysis Procedure
   (2-1) Case of Using Platelet Activating Agent
   (2-2) Case of Using Platelet Inactivating Agent
2. Blood Coagulation System Analyzing Device
   (1) Whole Configuration of Device
   (2) Analyzing Section
1. Blood Coagulation System Analyzing Method
(1) Measurement Procedure In the measurement procedure, the blood as the analysis subject (hereinafter, referred to as "sample blood") is held in a container including electrodes for applying a voltage to the blood, and an alternating current is applied to the electrodes to measure the complex permittivity of the sample blood.

In the present procedure, measurement about the sample blood is performed under a condition in which a substance that activates or inactivates the platelets is added and a condition in which the substance is not added. As the substance that activates the platelets (hereinafter, referred to as the "platelet activating agent"), adenosine diphosphate (ADP), collagen, arachidonic acid, epinephrine, ristocetin, thromboxane $A_2$ ($TXA_2$), adrenaline, etc. can be used. As the substance that inactivates the platelets (hereinafter, referred to as the "platelet inactivating agent"), acetylsalicylic acid, GPIIb/IIIa inhibitor, phosphodiesterase inhibitor, thienopyridine derivative, prostaglandin formulation, etc. can be used. Hereinafter, the platelet activating agent and the platelet inactivating agent will be referred to collectively as the "platelet activating agent etc."

Figure 1:
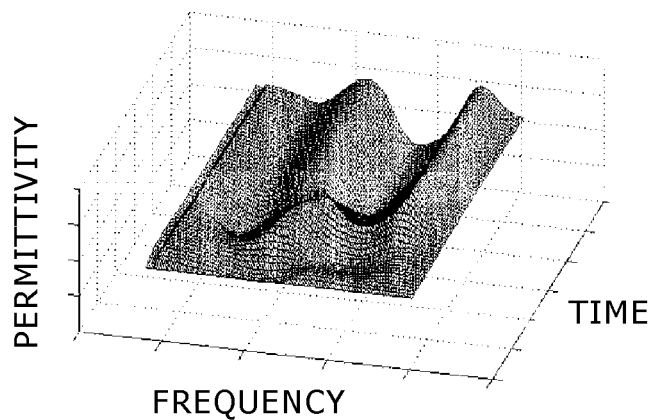
FIG. 1 is a drawing-substitute graph for explaining a measurement example of a complex permittivity spectrum (three-dimensional)
Figure 2:
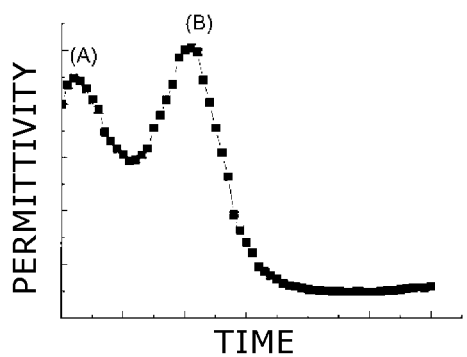
FIG. 2 is a drawing-substitute graph for explaining a measurement example of the complex permittivity spectrum (two-dimensional)

The measurement result can be obtained as a three-dimensional complex permittivity spectrum on a coordinate whose respective coordinate axes indicate the frequency, the time, and the permittivity (FIG. 1) or a two-dimensional complex permittivity spectrum on a coordinate whose respective coordinate axes indicate two selected from the frequency, the time, and the permittivity (FIG. 2). The Z-axis in the diagram indicates the real part of the complex permittivity at each time and each frequency.

FIG. 2 corresponds to a two-dimensional spectrum obtained by cutting out the three-dimensional spectrum shown in FIG. 1 at a frequency of 760 kHz. Symbol (A) in FIG. 2 shows a peak associated with rouleaux formation of red blood cells, and (B) shows a peak associated with the blood coagulation process.

The present inventors make it clear in the above-described Patent Document 1 that the time change of the permittivity of blood reflects the coagulation process of the blood. Therefore, the complex permittivity spectrum obtained by the present procedure serves as an index quantitatively indicating the coagulability of the blood, and information relating to the coagulability of the blood, such as the coagulation time, the coagulation rate, and the coagulation intensity, can be obtained based on a change in the complex permittivity spectrum.

Prior to the present procedure, the collection procedure of the sample blood is carried out in some cases. In the collection procedure, blood is collected from the person being tested as the analysis subject of the blood coagulation system in accordance with a normal method.
(2) Analysis Procedure In the analysis procedure, information relating to the coagulability of the sample blood is acquired based on the complex permittivity spectrum of the sample blood measured in the measurement procedure. Specifically, first, the complex permittivity spectrum measured about the sample blood to which the platelet activating agent etc. is added is compared with the complex permittivity spectrum measured about the sample blood to which it is not added. Then, information relating to the coagulability of the sample blood is acquired based on a change in the complex permittivity spectrum generated due to the addition of the platelet activating agent etc.

The complex permittivity spectrum measured about the sample blood to which the platelet activating agent etc. is not added will comprehensively reflect the blood coagulability involving plural factors. Specifically, the complex permittivity spectrum comprehensively reflects blood coagulation based on the aggregability of the platelets, blood coagulation based on the coagulation effect of plasma and blood cell component, and blood coagulation due to the influence of blood sedimentation that possibly occurs in the measurement. In the blood coagulation system analyzing method according to the embodiment of the present technique, particularly the information relating to the aggregability of the platelets can be picked out and acquired from these factors by using the platelet activating agent etc. The analysis procedure will be specifically described below about the case of using the platelet activating agent and the case of using the platelet inactivating agent separately.

(2-1) Case of Using Platelet Activating Agent

Figure 3:
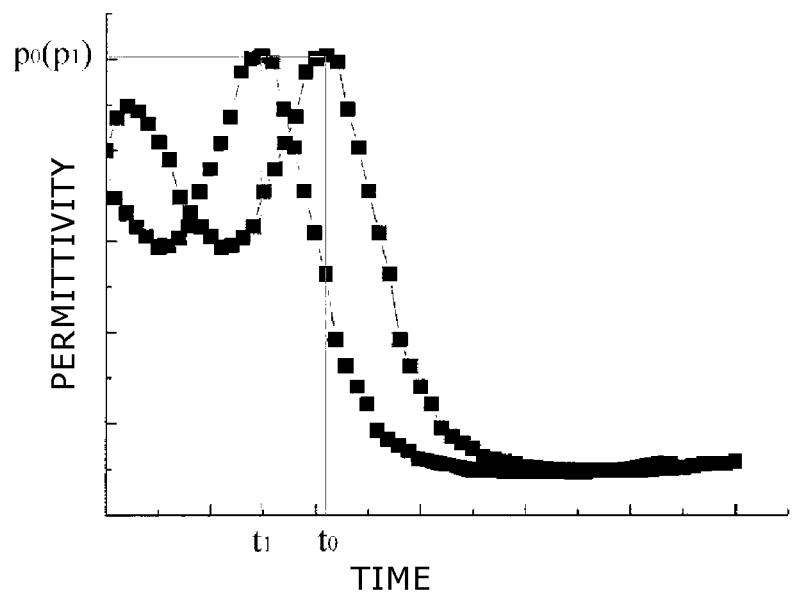
FIG. 3 is a drawing-substitute graph for explaining a change example of the complex permittivity spectrum when a platelet activating agent is added.

If the platelet activating agent is added to blood, the blood coagulation reaction is accelerated due to activation of the platelets and the blood coagulation time is shortened. Thus, in the complex permittivity spectrum of the blood to which the platelet activating agent is added, the time (blood coagulation time) t until a spectrum peak p associated with the blood coagulation appears is shortened compared with the complex permittivity spectrum of the blood to which the platelet activating agent is not added (see FIG. 3). In the diagram, symbols $p_0$ and $t_0$ indicate the spectrum peak and the blood coagulation time, respectively, when the platelet activating agent is not added. Symbols $p_1$ and $t_1$ indicate the spectrum peak and the blood coagulation time, respectively, when the platelet activating agent is added.

Therefore, according to the shortening width $\Delta t$ ($t_0$-$t_1$) of this blood coagulation time t, information about the degree of the aggregability of the platelets included in the sample blood in the inactive state can be obtained. Specifically, if the aggregability of the inactive platelets included in the sample blood is high, the blood coagulation reaction is greatly accelerated in the sample blood in which the platelets are activated by the platelet activating agent and the blood coagulation time is also greatly shortened. If the aggregability of the inactive platelets included in the sample blood is low, the reaction rate of the blood coagulation reaction hardly changes even when the platelets are activated by the platelet activating agent and thus shortening of the blood coagulation time is also not found.

If the shortening width $\Delta t_s$ of the blood coagulation time as the basis (reference value) is set by using blood known to have normal coagulability in advance, whether or not the aggregability of the platelets is good can be determined depending on whether the shortening width $\Delta t$ of the blood coagulation time of the sample blood is larger or smaller than $\Delta t_s$ (reference value). Specifically, it can be evaluated that the aggregability of the platelets is high if the shortening width $\Delta t$ of the blood coagulation time of the sample blood is larger than $\Delta t_s$ (reference value). Conversely, it can be evaluated that the aggregability of the platelets is low if the shortening width $\Delta t$ is smaller than $\Delta t_s$.

In a patient with platelet dysfunction or thrombocytopenia and a person who takes an anti-platelet aggregation drug such as the acetylsalicylic acid or an anticoagulant such as warfarin, heparin, or an activated blood coagulation factor X (Factor Xa) inhibitor, the aggregability of the platelets (hemostatic ability) is lowered and the bleeding risk increases. Therefore, for these patients and so forth, it is necessary to carry out disease management and medication management with timely evaluation of the aggregability of the platelets.

In the blood coagulation system analyzing method according to the embodiment of the present technique, the aggregability of the platelets can be easily evaluated based on a change in the complex permittivity spectrum due to addition of the platelet activating agent (specifically, shortening width $\Delta t$ of the blood coagulation time) as described above. Thus, the blood coagulation system analyzing method according to the embodiment of the present technique is useful for evaluating the platelet function of the patient with platelet dysfunction or thrombocytopenia. Furthermore, if the platelet function of a person who takes an anti-platelet aggregation drug or an anticoagulant is evaluated by using the blood coagulation system analyzing method according to the embodiment of the present technique, drug efficacy evaluation such as understanding of the excessive lowering of the coagulability due to excessive medication, the continuation of the hypercoagulable state due to dosage insufficiency, and so forth is also permitted.

In the above-described method, as a change in the complex permittivity spectrum, a change in the time (blood coagulation time) t until the spectrum peak p associated with the blood coagulation appears is used as an index for analysis. Furthermore, the aggregability of the platelets is evaluated based on the width $\Delta t$ of shortening of the blood coagulation time t due to addition of the platelet activating agent. In the blood coagulation system analyzing method according to the embodiment of the present technique, the change in the complex permittivity spectrum serving as an index for analysis is not particularly limited as long as it is a change in a feature extracted from the complex permittivity spectrum. Specific examples of the feature are shown below. Whether or not the aggregability of the platelets is good can be determined based on the reference value set in advance about the change width of these features and the width of a change generated in a feature extracted from the complex permittivity spectrum of the sample blood due to addition of the platelet activating agent.

Figure 4:
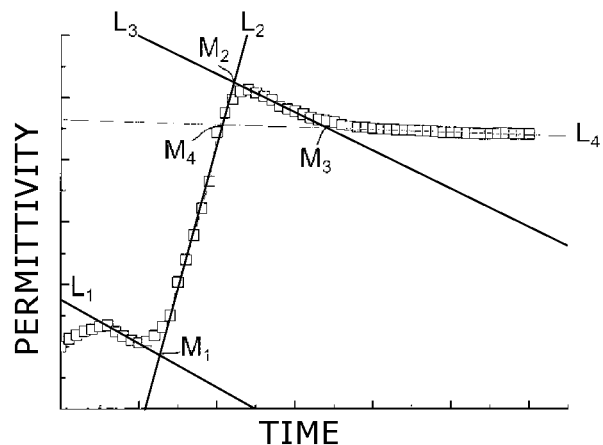
FIG. 4 is a drawing-substitute graph for explaining examples of the feature extracted from the complex permittivity spectrum (when the peak associated with a blood coagulation process is noticeable)
Figure 5:
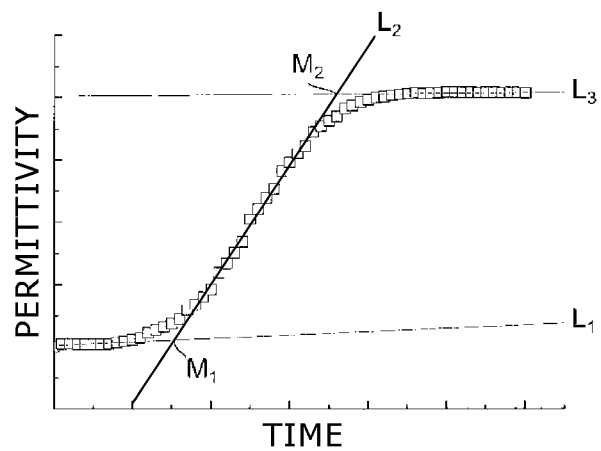
FIG. 5 is a drawing-substitute graph for explaining examples of the feature extracted from the complex permittivity spectrum (when the peak associated with the blood coagulation process is not noticeable)

The specific examples of the feature include extrapolated lines drawn on the curve indicating the complex permittivity spectrum (symbols $L_1$ to $L_4$ in FIG. 4 and FIG. 5), the coordinates of the intersections of the extrapolated lines (symbols $M_1$ to $M_4$), the slopes of the extrapolated lines, the slopes of tangents drawn on the curve indicating the complex permittivity spectrum (derivative value of the permittivity), a time T giving predetermined permittivity E (e.g. maximum value, local maximum value, intermediate value), and combinations of them. The specific examples of the feature further include a feature obtained by analyzing a three-dimensional complex permittivity spectrum as an image pattern, a feature obtained by parameter fitting with use of a function expression capable of reconfiguring the image pattern, and a feature obtained by cluster analysis with use of a large number of data among the spectrum data.

(2-2) Case of Using Platelet Inactivating Agent

Figure 6:
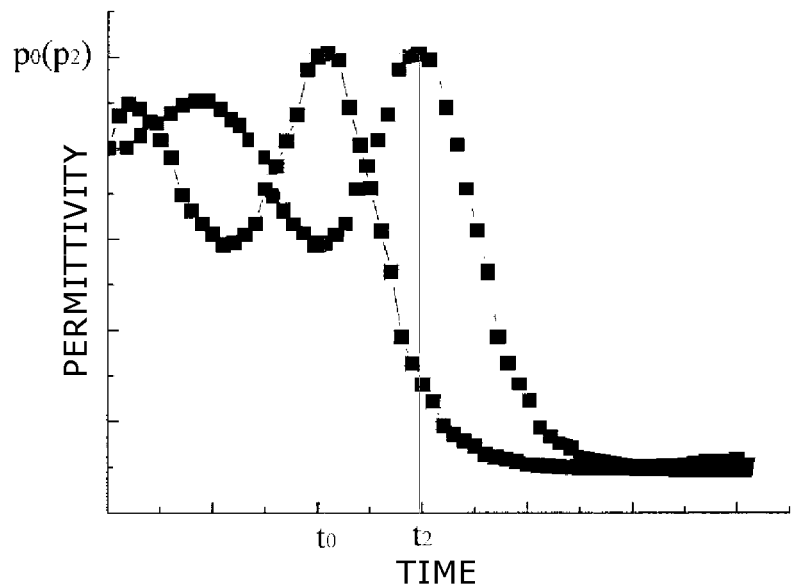
FIG. 6 is a drawing-substitute graph for explaining a change example of the complex permittivity spectrum when a platelet inactivating agent is added.

If the platelet inactivating agent is added to blood, the blood coagulation effect due to activated platelets included in the blood is suppressed, so that the coagulation reaction rate is lowered and the blood coagulation time is extended. Thus, in the complex permittivity spectrum of the blood to which the platelet inactivating agent is added, the time (blood coagulation time) t until the spectrum peak p associated with the blood coagulation appears is delayed compared with the complex permittivity spectrum of the blood to which the platelet inactivating agent is not added (see FIG. 6). In the diagram, symbols $p_0$ and $t_0$ indicate the spectrum peak and the blood coagulation time, respectively, when the platelet inactivating agent is not added. Symbols $p_2$ and $t_2$ indicate the spectrum peak and the blood coagulation time, respectively, when the platelet inactivating agent is added.

Therefore, according to the delay width $\Delta t$ ($t_2$-$t_0$) of this blood coagulation time t, information about the degree of the aggregability of the platelets included in the sample blood in the active state can be obtained. Specifically, if the blood coagulation time is greatly delayed due to addition of the platelet inactivating agent, it can be said that the aggregability of the platelets in the sample blood is high and a large amount of activated platelets are included in the sample blood. If the blood coagulation time hardly changes even when the platelet inactivating agent is added, it can be said that the aggregability of the platelets in the sample blood is low and activated platelets are hardly included in the sample blood.

If the delay width $\Delta t_s$ of the blood coagulation time as the basis (reference value) is set by using blood known to have normal coagulability in advance, whether or not the aggregability of the platelets is good can be determined depending on whether the delay width $\Delta t$ of the blood coagulation time of the sample blood is larger or smaller than $\Delta t_s$ (reference value). Specifically, it can be evaluated that the aggregability of the platelets is high if the delay width $\Delta t$ of the blood coagulation time of the sample blood is larger than $\Delta t_s$ (reference value). Conversely, it can be evaluated that the aggregability of the platelets is low if the delay width $\Delta t$ is smaller than $\Delta t_s$.

In the blood coagulation system analyzing method according to the embodiment of the present technique, the aggregability of the platelets can be easily evaluated based on a change in the complex permittivity spectrum due to addition of the platelet inactivating agent (specifically, delay width $\Delta t$ of the blood coagulation time) in this manner. Thus, the blood coagulation system analyzing method according to the embodiment of the present technique is useful for evaluating the platelet function of patients with diabetes and healthy people such as pregnant women having the risk of thrombosis and investigating how much the platelets that should not be activated originally are activated.

In the blood coagulation system analyzing method according to the embodiment of the present technique, the change in the complex permittivity spectrum serving as an index for analysis may be any as long as it is a change in a feature extracted from the complex permittivity spectrum, and is not limited to the delay width of the blood coagulation time as with the above description.

2. Blood Coagulation System Analyzing Device
(1) Whole Configuration of Device

Figure 7:
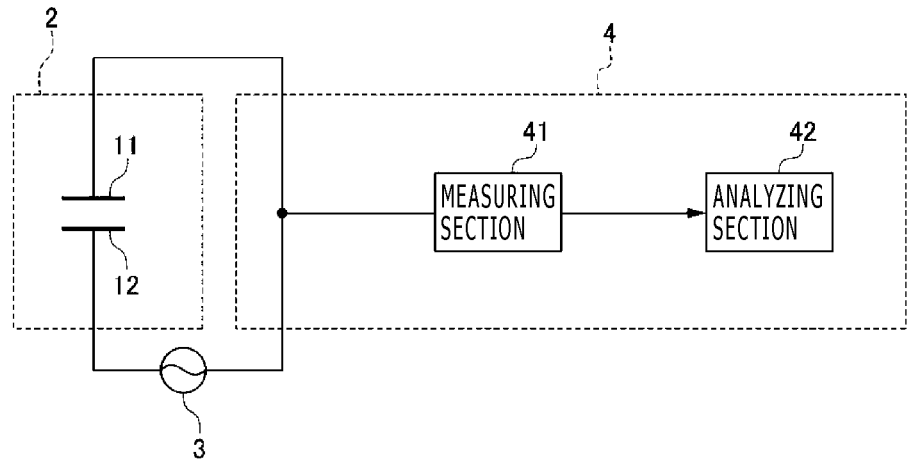
FIG. 7 is a schematic diagram for explaining the schematic configuration of a blood coagulation system analyzing device according to an embodiment of the present technique.

FIG. 7 shows the schematic configuration of a blood coagulation system analyzing device according to an embodiment of the present technique.

The blood coagulation system analyzing device includes a sample cartridge 2 to hold blood, a pair of electrodes 11 and 12 to apply a voltage to the blood held in the sample cartridge 2, a power supply 3 to apply an AC voltage to the electrodes 11 and 12, and a measuring section 41 to measure the permittivity of the blood. The measuring section 41 configures a signal processing section 4 together with an analyzing section 42 to receive the output of the measurement result from the measuring section 41 and determine the coagulability of the blood.

In the sample cartridge 2, a drug introduction port for adding the platelet activating agent etc. to the held blood may be provided. The blood may be housed in the sample cartridge 2 after being mixed with the platelet activating agent etc. in advance.

The power supply 3 applies the voltage from the timing when an order to start measurement is received or the timing when the power is turned on, as the start timing. Specifically, the power supply 3 applies an AC voltage having a predetermined frequency to the electrodes 11 and 12 at the set measurement interval.

The measuring section 41 measures the complex permittivity, the frequency dispersion thereof, and so forth from the timing when an order to start measurement is received or the timing when the power is turned on, as the start timing. Specifically, for example if the permittivity is measured, the measuring section 41 measures the current or impedance between the electrodes 11 and 12 at a predetermined cycle and derives the permittivity from the measurement value. For the derivation of the permittivity, known function and relational expression showing the relationship between the current or impedance and the permittivity is used.

To the analyzing section 42, data indicating the derived permittivity (hereinafter, referred to also as "permittivity data") is given from the measuring section 41 at the measurement interval. The analyzing section 42 starts determination of the coagulability of blood and so forth in response to the permittivity data given from the measuring section 41. The analyzing section 42 notifies one or both of the result of the coagulability determination and so forth and the permittivity data. This notification is performed e.g. by turning the information to a graph and displaying it on a monitor or printing it on a predetermined medium.

(2) Analyzing Section

A specific example of the determination step of the blood coagulability by the analyzing section 42 will be described below.

The analyzing section 42 executes processing of comparison between the complex permittivity spectrum measured about the sample blood to which the platelet activating agent etc. is added and the complex permittivity spectrum measured about the sample blood to which it is not added based on the permittivity data output from the measuring section 41. Furthermore, the analyzing section 42 determines the coagulability of the sample blood based on the difference in the spectrum pattern.

First, the analyzing section 42 compares the complex permittivity spectrum measured about the sample blood to which the platelet activating agent etc. is added and the complex permittivity spectrum measured about the sample blood to which it is not added. The comparison of the spectrum pattern can be performed based on a feature extracted from the complex permittivity spectra as the comparison subjects and the difference in the spectrum pattern can be detected from the difference in this feature. As the feature, e.g. the time until the spectrum peak associated with the blood coagulation appears (blood coagulation time) is used.

In this case, the analyzing section 42 determines whether or not the aggregability of the platelets is good depending on whether the shortening width (or delay width) $\Delta t$ of the blood coagulation time of the sample blood to which the platelet activating agent etc. is added is larger or smaller than the reference value ($\Delta t_s$). Specifically, the analyzing section 42 determines that the aggregability of the platelets is high if the shortening width $\Delta t$ of the blood coagulation time of the sample blood to which the platelet activating agent is added is larger than the reference value ($\Delta t_s$). Conversely, the analyzing section 42 determines that the aggregability of the platelets is low if the shortening width $\Delta t$ is smaller than the reference value ($\Delta t_s$). Alternatively, the analyzing section 42 determines that the aggregability of the platelets is high if the delay width $\Delta t$ of the blood coagulation time of the sample blood to which the platelet inactivating agent is added is larger than the reference value ($\Delta t_s$). Conversely, the analyzing section 42 determines that the aggregability of the platelets is low if the delay width $\Delta t$ is smaller than the reference value ($\Delta t_s$).

[Hypercoagulability]

If the blood coagulation time t of the sample blood to which the platelet activating agent etc. is not added is shorter than the reference value ($t_s$), the analyzing section 42 determines that the blood coagulability is high and notifies the result. This result can be displayed on a monitor and a predetermined medium as the risk of thrombosis.

In this case, if the shortening width $\Delta t$ of the blood coagulation time of the sample blood to which the platelet activating agent is added is larger than $\Delta t_s$ (reference value), the analyzing section 42 determines that the aggregability of the platelets is high and determines that the blood hypercoagulability is attributed to abnormal enhancement in the aggregability of the platelets. This determination result can be displayed on a monitor and a predetermined medium as the thrombosis risk due to abnormality in the platelet function.

On the other hand, if the shortening width $\Delta t$ of the blood coagulation time of the sample blood to which the platelet activating agent is added is smaller than $\Delta t_s$ (reference value), the analyzing section 42 determines that the aggregability of the platelets is low and determines that the blood hypercoagulability occurs independently of the platelet function. This determination result can be displayed on a monitor and a predetermined medium as the thrombosis risk due to abnormality in a factor other than the platelet function.

[Hypocoagulability]

Meanwhile, if the blood coagulation time t of the sample blood to which the platelet activating agent etc. is not added is longer than the reference value ($t_s$), the analyzing section 42 determines that the blood coagulability is low and notifies the result. This result can be displayed on a monitor and a predetermined medium as the risk of bleeding tendency.

In this case, if the shortening width $\Delta t$ of the blood coagulation time of the sample blood to which the platelet activating agent is added is smaller than $\Delta t_s$ (reference value), the analyzing section 42 determines that the aggregability of the platelets is low and determines that the blood hypocoagulability is attributed to abnormal lowering of the aggregability of the platelets. This determination result can be displayed on a monitor and a predetermined medium as the risk of bleeding tendency due to abnormality in the platelet function.

On the other hand, if the shortening width $\Delta t$ of the blood coagulation time of the sample blood to which the platelet activating agent is added is larger than $\Delta t_s$ (reference value), the analyzing section 42 determines that the aggregability of the platelets is high and determines that the blood hypocoagulability occurs independently of the platelet function. This determination result can be displayed on a monitor and a predetermined medium as the risk of bleeding tendency due to abnormality in a factor other than the platelet function.

In the above-described example, comparison of the spectrum pattern between the complex permittivity spectrum measured about the sample blood to which the platelet activating agent etc. is added and the complex permittivity spectrum measured about the sample blood to which it is not added is performed based on the time until the spectrum peak associated with blood coagulation appears (blood coagulation time). The feature for the comparison of the spectrum pattern is not particularly limited as long as it is a change in a feature extracted from the complex permittivity spectrum. Specific examples of the feature are shown below. The analyzing section 42 determines the coagulability of the sample blood based on the reference value retained in advance about the change width of these features and the width of a change generated in a feature extracted from the complex permittivity spectrum of the sample blood due to addition of the platelet activating agent etc.

The specific examples of the feature include extrapolated lines drawn on the curve indicating the complex permittivity spectrum (symbols $L_1$ to $L_4$ in FIG. 4 and FIG. 5), the coordinates of the intersections of the extrapolated lines (symbols $M_1$ to $M_4$), the slopes of the extrapolated lines, the slopes of tangents drawn on the curve indicating the complex permittivity spectrum (derivative value of the permittivity), a time T giving predetermined permittivity E (e.g. maximum value, local maximum value, intermediate value), and combinations of them. The specific examples of the feature further include a feature obtained by analyzing a three-dimensional complex permittivity spectrum as an image pattern, a feature obtained by parameter fitting with use of a function expression capable of reconfiguring the image pattern, and a feature obtained by cluster analysis with use of a large number of data among the spectrum data.

As described above, the blood coagulation system analyzing device according to the embodiment of the present technique determines whether or not blood hypercoagulability and hypocoagulability are present and determines also whether or not they are attributed to abnormality in the platelet function. Therefore, when the risk of thrombosis is suggested, important information for determining whether to perform antiplatelet therapy or to perform anticoagulation therapy is obtained by the blood coagulation system analyzing device according to the embodiment of the present technique.

Working Example

Test Example 1

1. Blood Coagulation System Analyzing Method with Use of Platelet Activating Agent The influence of addition of the platelet activating agent on the blood coagulability was studied by using sample blood of a healthy person and a patient with thrombocytopenia.
(1) Material and Method
(1-1) Blood Collection and Sample Preparation By using an evacuated blood collection tube treated with use of sodium citrate as an anticoagulant, blood was collected from the healthy person and the patient with thrombocytopenia (the number of platelets in 1 μL of blood was $1.2 \times 10^4$) as a whole blood sample.

Figure 8:
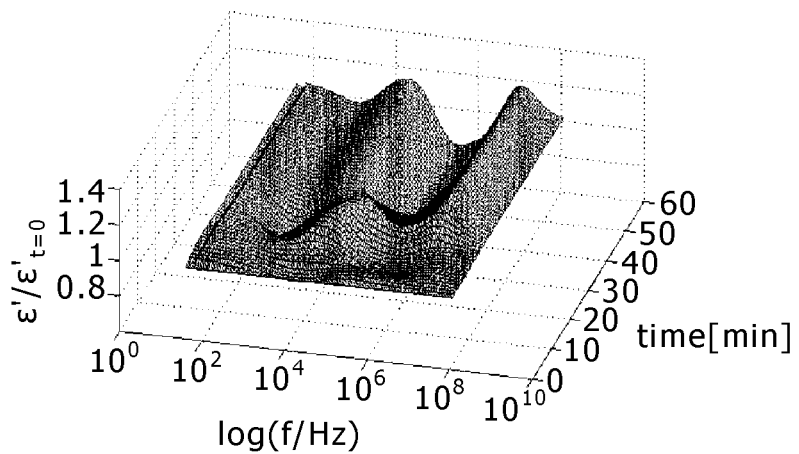
FIG. 8 is a drawing-substitute graph showing a dielectric response result of sample blood of a healthy person to which ADP (adenosine diphosphate) was not added (test example 1)
Figure 9:
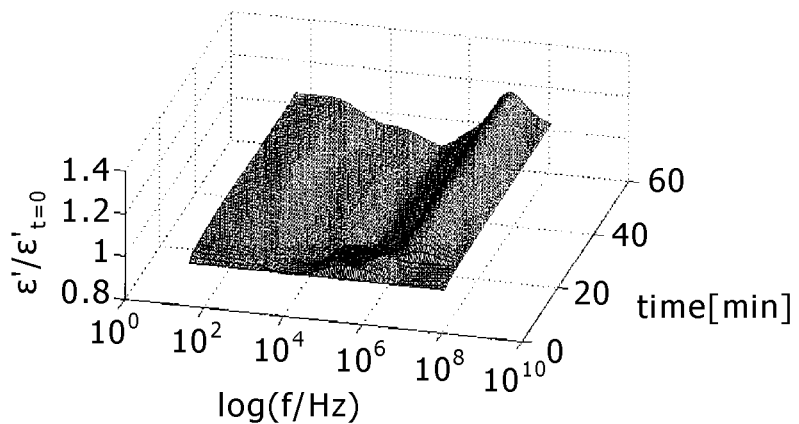
FIG. 9 is a drawing-substitute graph showing a dielectric response result of sample blood of a healthy person to which the ADP was added (test example 1)

Furthermore, blood cells and platelets were separated from the whole blood sample to prepare platelet poor plasma. The sample blood was centrifuged under a condition of 500 G and five minutes to be separated into blood cells and platelet rich plasma (PRP). The plasma was centrifuged under a condition of 2000 G and 30 minutes and sedimentation of the platelets was caused to obtain the platelet poor plasma (PPP).
(1-2) Dielectric Measurement Next, 0.25 M of a calcium chloride aqueous solution was added (85 μL per 1 mL of blood) to the sample blood whose temperature was kept at 37° C. and a blood coagulation reaction was started. The platelet activating agent (ADP) was so added as to be mixed in the calcium chloride aqueous solution (10 μM per 1 mL of blood). Immediately after the start of the blood coagulation reaction, measurement was performed for 60 minutes by using an impedance analyzer (Agilent Corporation, 4294A) under the following condition: temperature was 37° C.; frequency range was 40 Hz to 110 MHz; and measurement time interval was one minute.
(1-3) Measurement by Rheometer Measurement was performed by using a rheometer of the free damped oscillation type. The coagulation time was obtained by observing a change in the viscoelasticity and compared with the result by the dielectric measurement.
(2) Result FIG. 8 shows the dielectric response result of the sample blood of the healthy person to which the ADP was not added. FIG. 9 shows the dielectric response result of the sample blood of the healthy person to which the ADP was added. On the Z-axis in the diagrams, the real part of the complex permittivity at each time and each frequency is so shown as to be normalized by being divided by the real part of the complex permittivity at the time zero (immediately after measurement start) and each frequency. When comparison is made between FIG. 8 and FIG. 9, it turns out that the three-dimensional pattern of the dielectric response obviously changes due to the addition of the ADP.

Figure 10:
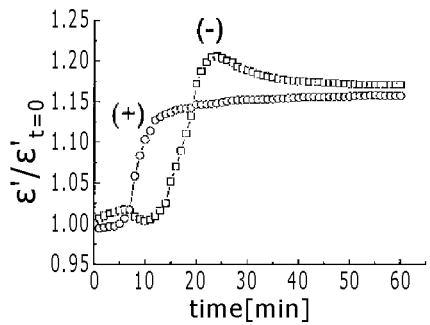
FIG. 10 is a drawing-substitute graph showing a change generated in the complex permittivity spectrum (frequency 10.7 MHz) of the sample blood of the healthy person due to the addition of the ADP (test example 1)

FIG. 10 shows the time change of the complex permittivity at a frequency of 10.7 MHz. Sign (−) indicates the dielectric response of the sample blood to which the ADP was not added, and sign (+) indicates the dielectric response of the sample blood to which the ADP was added. It turns out that, when the ADP was added, the step-like change in the permittivity corresponding to the blood coagulation was shifted toward the shorter time side compared with the case in which the ADP was not added. Such shortening of the coagulation time due to the ADP addition was observed in the sample blood of plural healthy persons in common. The average of the coagulation time when the ADP was added was 17 minutes and the average of the coagulation time when it was not added was 31 minutes.

Figure 11:
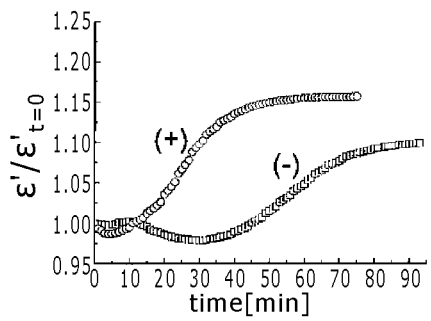
FIG. 11 is a drawing-substitute graph showing a change generated in the complex permittivity spectrum (frequency 10.7 MHz) of sample blood of a patient with thrombocytopenia due to the addition of the ADP (test example 1)

FIG. 11 shows the time change of the complex permittivity of the sample blood of the patient with thrombocytopenia at a frequency of 10.7 MHz. Sign (−) indicates the dielectric response of the sample blood to which the ADP was not added, and sign (+) indicates the dielectric response of the sample blood to which the ADP was added. Although shortening of the coagulation time was found due to the ADP addition, the coagulation time was 38 minutes. Thus, it turns out that this time was obviously longer than the average of the coagulation time of the healthy person, 17 minutes. This will be because the number of platelets in the sample blood was small and therefore promotion of the blood coagulation reaction by the ADP was limited.

Figure 12:
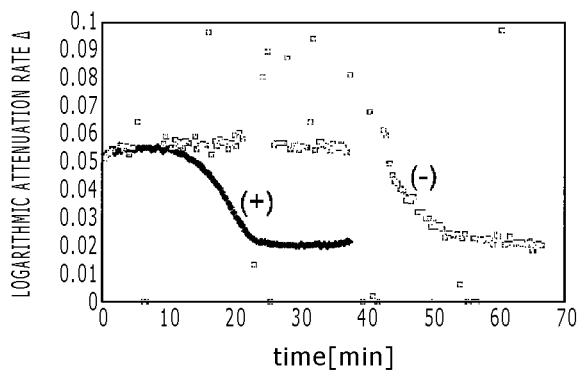
FIG. 12 is a drawing-substitute graph showing a viscoelasticity change of sample blood of a healthy person to which the ADP was added and to which it was not added, measured by a rheometer (test example 1)
Figure 13:
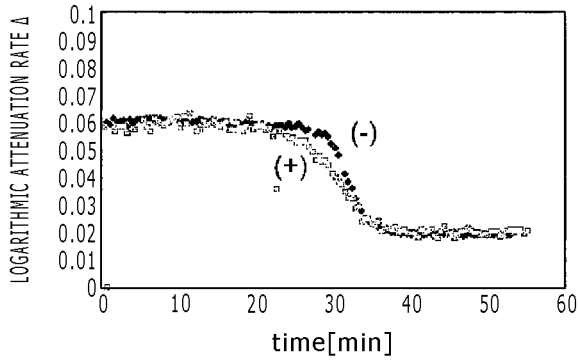
FIG. 13 is a drawing-substitute graph showing a viscoelasticity change of platelet poor blood to which the ADP was added and to which it was not added, measured by the rheometer (test example 1).

FIG. 12 and FIG. 13 show the result of the complementary experiment by the rheometer. FIG. 12 shows the time change of the viscoelasticity of the sample blood of the healthy person to which the ADP was added (+) and to which it was not added (−). FIG. 13 shows the time change of the viscoelasticity when the ADP was added to platelet poor blood obtained by adding cleaned red blood cells to the separated platelet poor plasma (PPP) (+) and when it was not added (−). In the experiment with use of the sample blood of the healthy person, shortening of the coagulation time due to the ADP addition was found as with the result by the dielectric measurement. In contrast, in the experiment with use of the platelet poor blood, a change in the coagulation time due to the ADP addition was not observed.

From the result of the above-described present test example, it is revealed that the aggregability of the platelets in the sample blood can be easily evaluated based on a change in the complex permittivity spectrum generated due to addition of the platelet activating agent.

By the blood coagulation system analyzing method according to the embodiment of the present technique, whether or not blood hypercoagulability and hypocoagulability are present can be determined and whether or not they relate to the aggregability of the platelets can be determined. This method is useful for evaluating the thrombus risk of patients with diabetes, arteriosclerosis, cancer, heart disease, respiratory disease, and so forth, perioperative patients, patients currently taking an immunosuppressant, pregnant women, elderly people, etc. Furthermore, in prophylactic medication of an anti-platelet aggregation drug or an anticoagulant for these patients and healthy people, this method can be used also for evaluating the risk of bleeding tendency due to excessive administration.

The present application contains subject matter related to that disclosed in Japanese Priority Patent Application JP 2011-058810 filed in the Japan Patent Office on Mar. 17, 2011, the entire content of which is hereby incorporated by reference.

It should be understood by those skilled in the art that various modifications, combinations, sub-combinations and alterations may occur depending on design requirements and other factor in so far as they are within the scope of the appended claims or the equivalents thereof.

What is claimed is:

1. A method for analyzing blood coagulation comprising:
adding a substance that activates platelets into a blood sample to initiate a coagulation process of the blood sample;
obtaining a complex permittivity spectrum in the coagulation process of the blood sample;
determining a change of at least one parameter of the measured complex permittivity spectrum with respect to that of a reference complex permittivity spectrum of the blood sample without the substance;
comparing the change with a reference value; and
acquiring information relating to coagulability of the blood sample based on the comparison,
wherein,
the information includes data relating to an aggregability of the platelets included in the blood sample in an inactive state.

2. The method according to claim 1, wherein:
the blood sample is collected from a subject to which an anti-platelet aggregation drug is administered, and
drug efficacy of the anti-platelet aggregation drug is evaluated based on the change.

3. The method according to claim 2, wherein the anti-platelet aggregation drug is acetylsalicylic acid.

4. The method according to claim 1, wherein:
the blood sample is collected from a subject to which an anticoagulant is administered, and
drug efficacy of the anticoagulant is evaluated based on the change.

5. The method according to claim 4, wherein the anticoagulant is selected from warfarin, heparin, and an activated blood coagulation factor X inhibitor.

6. The method according to claim 1, wherein:
the blood sample is collected from a subject to which an anti-platelet aggregation drug and an anticoagulant are administered, and
drug efficacy of the anti-platelet aggregation drug and the anticoagulant is evaluated based on the change.

7. The method according to claim 6, wherein:
the anti-platelet aggregation drug is acetylsalicylic acid, and
the anticoagulant is selected from warfarin, heparin, and an activated blood coagulation factor X inhibitor.

8. The method according to claim 1, wherein the substance includes calcium chloride.

9. The method according to claim 1, wherein the reference value is set by a reference blood sample that is known to have normal coagulability.

10. A method for analyzing blood coagulation comprising:
adding a substance that inactivates platelets into a blood sample to initiate a coagulation process of the blood sample;
obtaining a complex permittivity spectrum in the coagulation process of the blood sample;
determining a change of at least one parameter of the measured complex permittivity spectrum with respect to that of a reference complex permittivity spectrum of the blood sample without the substance;
comparing the change with a reference value; and
acquiring information relating to coagulability of the blood sample based on the comparison,
wherein,
the information includes data relating to aggregability of the platelets included in the blood sample in an active state.

11. A device for analyzing blood coagulation comprising:
a coagulation section configured to add a substance that activates platelets into a blood sample to initiate a coagulation process of the blood sample;
a measurement section configured to obtain a complex permittivity spectrum in the coagulation process of the blood sample; and
an analyzing section configured to (a) determine a change of at least one parameter of the measured complex permittivity spectrum with respect to that of a reference complex permittivity spectrum of the blood sample without the substance; (b) compare the change with a reference value, and (c) determine information relating to coagulability of the blood sample based on the comparison,
wherein,
the information includes data relating to an aggregability of the platelets included in the blood sample in an inactive state.

12. A device for analyzing blood coagulation comprising:
a coagulation section configured to add a substance that inactivates platelets into a blood sample to initiate a coagulation process of the blood sample;
a measurement section configured to obtain a complex permittivity spectrum in the coagulation process of the blood sample; and
an analyzing section configured to (a) determine a change of at least one parameter of the measured complex permittivity spectrum with respect to that of a reference complex permittivity spectrum of the blood sample without the substance; (b) compare the change with a reference value, and (c) determine information relating to coagulability of the blood sample based on the comparison
wherein,
the information includes data relating to an aggregability of the platelets included in the blood sample in an active state.

13. The device according to claim 12, wherein the reference value is set by a reference blood sample that is known to have normal coagulability.

* * * * *